(12) United States Patent
Plank et al.

(10) Patent No.: US 7,732,000 B2
(45) Date of Patent: Jun. 8, 2010

(54) FOOD INTERMEDIATE HAVING SEQUESTERED PHYTOSTERYL ESTERS IN A POLYSACCHARIDE MATRIX

(75) Inventors: David W. Plank, Taylors Falls, MN (US); Daniel J. Lewandowski, Bloomington, MN (US); Barrie R. Froseth, Plymouth, MN (US); Jonathan W. Devries, Coon Rapids, MN (US)

(73) Assignee: General Mills, Inc., Minneapolis, MN (US)

( * ) Notice: Subject to any disclaimer, the term of this patent is extended or adjusted under 35 U.S.C. 154(b) by 734 days.

(21) Appl. No.: 10/176,822

(22) Filed: Jun. 20, 2002

(65) Prior Publication Data

US 2003/0235643 A1 Dec. 25, 2003

(51) Int. Cl.
*A21D 2/08* (2006.01)
(52) U.S. Cl. ..................................... 426/549; 426/611
(58) Field of Classification Search .................. 426/601, 426/549, 611, 573, 577
See application file for complete search history.

(56) References Cited

U.S. PATENT DOCUMENTS

| | | | |
|---|---|---|---|
| 3,881,005 A * | 4/1975 | Thakkar et al. ............. | 514/182 |
| 5,244,887 A | 9/1993 | Straub | |
| 5,747,464 A * | 5/1998 | See .............................. | 514/26 |
| 6,136,349 A | 10/2000 | Karppanen et al. | |
| 6,174,560 B1 | 1/2001 | Miettenen et al. | |
| 6,423,363 B1 * | 7/2002 | Traska et al. ................. | 426/604 |
| 6,677,327 B1 * | 1/2004 | Gottemoller ................. | 514/182 |
| 2002/0006461 A1* | 1/2002 | Haarasilta et al. | |
| 2002/0012733 A1* | 1/2002 | Kester et al. | |
| 2002/0183530 A1* | 12/2002 | Aaltonen et al. ............. | 552/545 |
| 2003/0068357 A1* | 4/2003 | Vala et al. | |
| 2003/0165572 A1* | 9/2003 | Auriou | |
| 2004/0028795 A1* | 2/2004 | Doat et al. ................... | 426/601 |

FOREIGN PATENT DOCUMENTS

| | | | |
|---|---|---|---|
| EP | 0947197 | * | 6/1999 |
| GB | 934686 | * | 3/1962 |
| JP | 020299548 | * | 2/1990 |
| JP | 2-299548 | * | 11/1990 |
| WO | WO95/00158 | * | 1/1995 |
| WO | WO 99/39715 | * | 8/1999 |
| WO | WO 01/30359 | * | 10/1999 |

OTHER PUBLICATIONS

Lee, Frank. 1975. Basic Food Chemistry. The AVI Publishing Co., Inc., Westport, CT. p. 17, 18, 31, 32.*
Hoseney, R. C. 1986. Principles of Cereal Science and Technology, 2nd edition, Am. Assoc. of Cereal Chemists, Inc, St Paul Minnesota, p. 12, 35-39, 44-47, 264-265.*
Pomeranz, Y. 1988. Wheat: Chemistry and Technology, vol. 1, Am. Assoc of Cereal Chemists, Inc, St. Paul, Minnesota, p. 375, 388-397.*
Potter, N. N. 1973. Food Science, 2nd edition, The AVI Publishing Co., Inc., Westport, CT. p. 464.*
Desrosier, N. W. 1977. Elements of Food Technology. AVI Publishing Co., Inc., Westport, CT. p. 147.*
Lee, F. A. Basic Food Chemistry. AVI Publishing Co., Inc. Westport, CT., p. 17.*
21 CFR 101.83, Edition 4-1-01. p. 147-150.*
"Health claims: plant sterol/stanol esters and risk of coronary heart disease." FDA, 21CFR101.83 (2004).
"Plant sterol and stanol margarines and health." Malcolm Law, BMJ, vol. 320 pp. 861-864 (2000).

* cited by examiner

*Primary Examiner*—Carolyn A Paden
(74) *Attorney, Agent, or Firm*—Dale A. Bjorkman; John A. O'Toole

(57) ABSTRACT

The present invention is related to a novel food intermediate containing a phytosteryl esters complex and the method used to create the food intermediate. The food product provides beneficial hypocholesterolemic activity through increased cholesterol-uptake inhibition while simultaneously delivering a food product that is not adversely affected by its inclusion, either in taste or texture or in any undesirable side effects.

8 Claims, 2 Drawing Sheets

FOOD INTERMEDIATE HAVING SEQUESTERED PHYTOSTERYL ESTERS IN A POLYSACCHARIDE MATRIX

CROSS-REFERENCES TO RELATED APPLICATIONS

None.

BACKGROUND OF THE INVENTION

The present invention is related to a novel food intermediate containing phytosteryl esters complex and the method used to create the food intermediate. The food product provides beneficial hypocholesterolemic activity through cholesterol-uptake inhibition while simultaneously delivering a food product, which is not adversely affected by its inclusion, either in taste or texture or in any undesirable side effects.

There is a large amount of information in circulation today concerning elevated cholesterol levels and the health consequences due to that condition. In an effort to combat this result, a number of pharmaceutical applications, dietary supplements and other solutions relating to the treatment of high cholesterol levels have been previously introduced. However, regrettably, many of these products have an unpleasant mouth feel, that is they can feel slimy, have a displeasing taste or result in undesirable side effects which diminishes their overall value to the intended end user.

In addition, there also appears to be a growing disdain against ingesting some sort of dietary supplement, pharmaceutical treatment or other product to attain some perceived beneficial effect from such products. This may be due to a growing reliance on pills or tablets to sustain or maintain our health. Such reliance on supplements may also surprisingly contribute to malnutrition as other valuable vitamins and minerals can be omitted or overlooked when too much focus is diverted to certain items. Moreover, certain supplements may actually remove valuable macronutrients and micronutrients from the system. Individuals may also be concerned with potential risks and side effects associated with certain medications, treatments or supplements. In fact, dietary restrictions and other health concerns may preclude certain portions of the population from even consuming such products. As such, there remains a continuing interest in developing good tasting, well balanced, food products that contribute to a well balanced diet as well as provide a vehicle by which to deliver the benefit of cholesterol reduction in a palatable and efficient manner to meet the changing needs of the population.

Cholesterol in humans is known to come from primarily two sources, the body's own production of cholesterol (endogenous) and dietary cholesterol (exogenous). Lipoproteins contain specific proteins and varying amounts of cholesterol, triglycerides and phospholipids.

Bile acids are synthesized from cholesterol in the liver and then secreted into the intestines. Reducing the level of bile acid reabsorption facilitates the maintenance of a healthy cholesterol level. One method for reducing bile acid reabsorption is achieved by increasing the gut viscosity. Alternatively, a non-digestible dietary component, which binds bile acids secreted in the proximal jejunum, will reduce bile acid reabsorption in the lower intestines (distal ileum).

There are three major classes of lipoproteins and they include very low-density lipoproteins ("VLDL"), low-density lipoproteins ("LDL") and high-density lipoproteins ("HDL"). The LDLs are believed to carry about 60-70% of the serum cholesterol present in an average adult. The HDLs carry around 20-30% of serum cholesterol with the VLDL having around 1-10% of the cholesterol in the serum. To calculate the level of non-HDL cholesterol present (find the level of LDL or VLDL levels), which indicates risk; the HDL is subtracted from the total cholesterol value.

Typically, the average person consumes between 350-400 milligrams of cholesterol daily, while the recommended intake is around 300 milligrams. Increased dietary cholesterol consumption, especially in conjunction with a diet high in saturated fat intake, can result in elevated serum cholesterol. Having an elevated serum cholesterol level is a well-established risk factor for heart disease and therefore there is a need to mitigate the undesired effects of cholesterol accumulation. High cholesterol levels are generally considered to be those total cholesterol levels at 200 milligrams and above or LDL cholesterol levels at 130 milligrams and above. By lowering the total system LDL cholesterol level, it is believed that certain health risks, such as coronary disease and possibly some cancers, that are typically associated with high cholesterol levels, can be reduced by not an insignificant amount.

Numerous studies relating to modifying the intestinal metabolism of lipids have been done to illustrate that such effects can reduce a high cholesterol level. Hampering the absorption of triglycerides, cholesterol or bile acids or a combination of these items results in a lowering of cholesterol levels in the serum.

It has been suggested that phytosterols specifically displace cholesterol from the micelles in the small intestine (micelles are amphiphyllic droplets secreted from the liver through the bile ducts into the small intestine). Micelles are composed primarily of bile acids, phosphatidyl choline, and lipids and are responsible for the solubilization of fats and cholesterol from ingested food. Micelles are reabsorbed by the body along with the solubilized fats and cholesterol. Phytosterols displace cholesterol from the micelles and thus decrease cholesterol uptake and the concomitant serum cholesterol levels of the organism. In humans the phytosterols that are taken up with the micelles are transported back into the intestine where it is excreted.

Soluble dietary fiber is known to be a safe ingredient due to its long history in food supply. Soluble fiber typically remains undigested, except by colonic microflora present in the lower intestines. Soluble dietary fiber is believed to have a beneficial effect in the reduction of high serum cholesterol levels and reducing the risk associated with such elevated levels. In addition, soluble dietary fiber can have the additional beneficial effect of reduced constipation and improved regularity. However, too much fiber in the diet can create undesirable gastrointestinal side effects such as flatulence, diarrhea, and abdominal cramps, etc. leading consumers to stay away from food products that contain too much dietary fiber, regardless of any associated health benefits. While some consumers may not completely avoid such products, they also do not typically regularly use such products due to the problems enumerated above or alternatively, or in combination due to the unpleasant taste of such products. This illustrates some of the problems with prior solutions that were aimed at providing high fiber diets directed at lowering cholesterol levels, and highlights the need to create a more balanced solution that fits not only within more normal dietary patterns but also meets consumer demand for better tasting, healthy products.

There are a number of other products purporting to have cholesterol-lowering properties available in the market today. One such product offering or solution is described in U.S. Pat. No. 6,136,349 which relates to a food product, food additive or the like that may be fortified with a select group of minerals, such as calcium, magnesium or potassium which when combined with conventional sterols and/or stanols increases the effect of the sterols and/or stanols in lowering cholesterol levels than with just sterols an/or stanols alone. However, significantly increasing only certain nutrients and minerals while ignoring others can result in over consumption or under consumption of essential nutrients because some nutrients are present in very high concentrations while other nutrients are present in very low concentrations. This creates a nutritionally unbalanced situation causing the consumer to either procure the missing macro and/or micronutrients through other food sources or omit them from their diet altogether. In addition to not receiving the DV (Daily Value) of certain nutrients, this may force the consumer into an over compensation mode causing the consumer to ingest more food than is actually necessary thereby defeating the purpose of such cholesterol-lowering foods, and potentially create other problems such as weight gain.

Another possible solution is described in U.S. Pat. No. 6,174,560, which relates to a food composition for lowering low-density cholesterol levels (LDL) and focuses on the use of at least one stanol fatty acid ester in combination with a nutritional substance. The applicants of U.S. Pat. No. 6,174,560 however indicates that increasing the amount of fiber to reduce serum cholesterol levels has been of a limited effect and citing that fiber that is delivered in therapeutically effective doses, such as with pharmaceutical applications, can cause extreme abdominal discomfort. This provides another singular example of a particular element or component being relied upon for a health effect but still ignoring the combined beneficial effects of the present invention as well as the ability to deliver the food product in an acceptable manner.

U.S. Pat. No. 5,244,887 describes the use of stanols as food additives to reduce cholesterol absorption. In the preparation of the additives, sitostanol is dissolved with an edible solubilizing agent such as triglyceride, an antioxidant such as tocopherol, and a dispersant such as lecithin, polysorbate 80, or sodium lauryl sulfate. However, no data is provided in the selection of the most effective components and their amounts or specific methods of preparation. Effectiveness in reducing cholesterol absorption was also not determined. The preferred embodiment consisted of 25% by weight stanols in vegetable oil, but the solubility of sterols in oil is only 2%.

One of the difficulties in attempting to deliver phytosterols in a food intermediate is that the phytosterols may be oxidized or otherwise degraded during the cooking process, thus destroying the beneficial properties of including such components in food. In order to overcome this drawback, manufacturers have attempted to manipulate the cooking/processing cycles however, this results in producing products which do not have the same quality as other products that were created using well established processes.

Therefore, what is needed is an effective method of delivering phytosterols in a food product in order to obtain the beneficial hypocholesterolemic activity associated with such ingredients.

Publications, patents and patent applications are referred to throughout this disclosure. All references cited herein are hereby incorporated by reference.

BRIEF SUMMARY OF THE INVENTION

In one preferred embodiment of the present invention, a food intermediate having enhanced cholesterol-uptake inhibition is described and comprises a polysaccharide and a phytosterol based component. The phytosterol-based component is bound in a matrix with the polysaccharide to create a complex containing the phytosterol based component and the polysaccharide. The food intermediate contains the complex.

In another embodiment of the present invention, a method of making a food intermediate having enhanced cholesterol-uptake inhibition is described and comprises the steps of, providing a source of polysaccharide having a chain length ranging between 5 to 1,000,000 glucose units. A phytosterol based component is provided and then the polysaccharides and phytosterol based component are mixed together. The mixture is then heated to create a complex containing the phytosterol based component bound to the polysaccharides. Finally, the complex is added to other pre-selected ingredients to make a food intermediate.

In a still further embodiment of the present invention, a complex for delivering phytosterols and fatty acid derivatives thereof (phytosteryl esters) for inclusion into a food intermediate having beneficial cholesterol-uptake inhibition, is described and comprises, a source of polysaccharides obtained from a grain. The complex also includes a source of a phytosterol based component which is mixed with the source of polysaccharides. In order to form the complex, the mixture containing the source of polysaccharides and the phytosterol based component is heated to bind the phytosterol based component to the source of polysaccharides to create a complex having enhanced cholesterol-uptake inhibition.

In a further embodiment of the present invention, a method of communicating a benefit associated with a food intermediate having enhanced cholesterol-uptake inhibition, is disclosed and comprises the steps of initially obtaining results from a study using a food intermediate incorporated into a food product having a complex created by mixing and heating a phytosterol based component with a polysaccharide. Then producing a draft message concerning the results of the study and finally imaging the message on a product package indicating that a diet which includes the food intermediate containing the complex results in a amount of cholesterol reduction.

BRIEF DESCRIPTION OF THE DRAWINGS

The forgoing, as well as other objects and advantages of this invention, will be more completely understood and appreciated by referring to the following more detailed description of the presently preferred exemplary embodiments of the invention in conjunction with the accompanying drawings, of which.

DETAILED DESCRIPTION OF THE INVENTION

Figure 1:
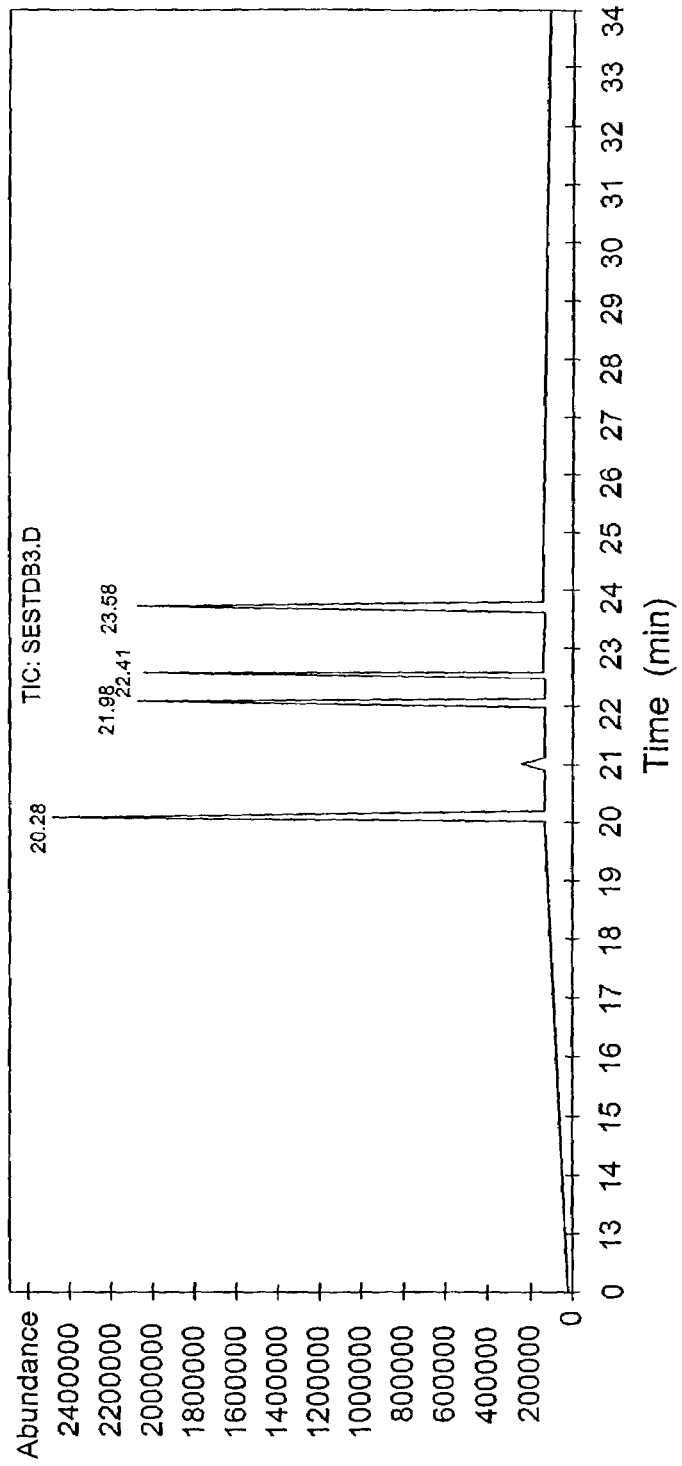
FIG. 1 is a gas chromatograph illustrating sterol standards.

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

Sterols occur in natural fats and oils, particularly in vegetable oils. Unsaturated vegetable oils and non-animal fat oils, such as soybean oil, wheat germ oil, cottonseed oil, safflower oil, peanut oil, rice oil, canola oil and the like are well known sources of β-sitosterol, stigmasterol, ergosterol and campesterol as well as various other materials such as higher aliphatic alcohols. Tall oil is also a significant source of β-sitosterol and campesterol.

Stanols (β-sitostanol, campestanol, stigmastanol and fatty acid derivatives thereof) are the 5 alpha saturated derivatives of plant sterols and may be derived from similar sources set forth above.

Natural plant sterols are similar structurally to cholesterol except in the arrangement of the basic side chains. Absorption of plant sterols in the intestines is believed to be minimal at best and sterols/steroids are generally excreted in the stool. Thus, the levels of plant sterols in the serum remain relatively low since they are minimally absorbed by the body and are generally quickly excreted. Where the amount of sterols is increased in an effort to obtain greater beneficial or health effects, the sterols still do not increase significantly in amount in the blood serum as the absorption capability, however limited it may be, is quickly exceeded. As such, by including sterol related or containing compounds in food products, food ingredients, food intermediates and food components, the level of cholesterol-uptake is inhibited while the level of sterols in the blood serum is not significantly elevated and hence, due to reduced uptake, cholesterol levels decrease.

Polysaccharides, which comprise a number of glucose units linked together in a polymer fashion to form chains of varying length, as used herein have a chain length ranging between 5 to 1,000,000 glucose units, preferably 5,000 to 500,000 units and more preferably from 20,000 to 100,000 glucose units. Exemplary polysaccarides include starches, cellulose and glycogen.

Pectins are polymeric chains of partially methylated galacturonic acids that possess the ability to form a gel in water. A preferred polysaccharide of the present invention is amylopectin which is branched molecule.

Another preferred polysaccharide is beta glucan, particularly grain beta glucans (oats and barley), which are a known source of dietary fiber and have been included in food products that are used in weight control (beta glucans used as fat substitutes) and as cholesterol lowering additives. Beta glucans are obtained from milled cereal grains such as oats and barley (waxy, hulless barley being a particularly good source) in a manner discussed above and are then extracted from the milled grains into warm water and then the solids are removed from the solution.

Beta glucan is a naturally occurring polysaccharide that can be found, in the cell walls of cereal grains. Beta glucan, or beta 1-4/1-3 glucosyl pyranose polymer, is a chain of (1-4) and (1-3) linked glucose molecules that is staggered, having a beta (1-3) linkage after 4-6 beta (1-4) linkages. This results in a laminated macromolecule. This general beta glucan structure will continue for 20,000 to 100,000 glucose units. The laminations allow water molecules to fit between the beta (1-4) layers which allows beta glucan to hydrate.

The beta glucans that are used in this invention can be naturally occurring or be chemically or enzymatically modified by altering the specific linkages. Methods for extracting and purifying beta glucan, for example, from the cell walls of cereal grains, have been developed and an exemplary method is described in commonly assigned application Ser. No. 10/067,016 filed Feb. 4, 2002 the disclosure of which including that found in the claims is incorporated herein by reference.

In a preferred embodiment, a starch containing food product, such as a ready to eat ("RTE") cereal is prepared in a conventional manner. Examples of RTE cereals include CHEERIOS® and WHEATIES® available from General Mills, Minneapolis, Minn.

Food intermediates such as dough, comprise a mixture of a flour and a liquid component (e.g. water). Such doughs can also optionally include a broad variety of other ingredients, as is generally known (e.g. salt, seasoning, leaving agents, etc.). Dough can be used to make a broad variety of food products, for example, ready to eat cereals, snack foods, breads, rolls, other assorted baked goods, and a variety of other foods.

The flour or meal used to make a dough intermediate are preferably grain based flours or meals that contribute to the structure, texture, taste and appearance of the dough. The flour or meal can be based upon a broad variety of grains, for example, oat, wheat, corn, rice, rye, barley, mixtures thereof, and other such flours or meals and mixtures thereof. In some examples, the flour or meal can be de-fatted, but such embodiments are not necessarily preferred. Preferably, the flour or meal is oat, wheat or corn based, for example an oat, corn or wheat flour. More preferably, the oat based flour is used.

Additional optional ingredients can be used to modify the properties of the dough, such as the taste, texture, structure, and appearance of the dough. Examples of such additional ingredients include fats or shortening agents, surfactants/emulsifiers, hydrocolloids, salts, sugars and other sweeteners, dough developing agents, texture agents, enzymes, fillers, eggs, leavening agents, flavor enhancing additives, coloring additives, nutritional supplements, preservatives, mold inhibitors and other such ingredients.

In a preferred embodiment of the present invention, oat flour is used and is essentially beat-treated oat groats (hulled, crushed oats) or rolled oats that are ground on a hammer mill or other smooth rolls. There is no separation of the components during the processing of the flour.

The phytosterols, which are selected the group consisting of β-sitosterol, stigmasterol, ergosterol and campesterol, and fatty acid derivatives thereof, are bound in a complex with the polysaccharide, preferably, amylopectin, by heating the phytosterol/phytosteryl ester in a mixture containing the polysaccharide. The complex may then be dried by a number of known methods and is then added to the flour that is then processed into the dough. Thus, the complex created by the present invention forms an effective delivery vehicle for phytosterols and their esters.

With reference to the term "mixture" as used herein, the mixture can be made in an aqueous solution or simply by mixing the phytosterols and/or phytosteryl esters together with the polysaccharide with no other substances creating a "neat" mixture.

In one example, amylopectin and β-sitosterol oleate are added to an aqueous solution. The solution is heated/cooked in order to create a bound steryl-ester that is generally inaccessible to extraction and saponification.

By creating a complex between the phytosterols and polysaccharides in this manner, it has been found that the phytosterols do not undergo the degradation or oxidation where the phytosterols are added separately and remain generally uncomplexed during the processing of the food intermediate. Thus, the sequestered steryl ester will be delivered to the location in the gut where it will be most efficacious. On entry to the small intestine, the complex is exposed to micelles which mimic the action of an organic solvent. It is presumed that the displacement of the sterol ester from the complex that provides the enhanced bile acid binding capacity and hence the cholesterol lowering benefit.

Surprisingly, it has been found that the complex formed by the instant invention does not adversely affect the taste or texture of the product into which it is being incorporated. In addition, it is believed that the complex of the present invention provides an improved mouth feel and texture to the product in which it is used. This represents an improvement over prior solutions that have appeared or tasted slimy.

In the present invention, between 1 and 10 grams of sterols are provided per serving in the above-described matrix and more preferably, about 2-6 grams per 30 gram serving, or approximately 10 to 20% by weight. Where the serving size is approximately 55 grams, the amount of sterols per serving would be in the range of roughly 3 to 12 grams. Obviously, other derivations are possible.

For the presently described exemplary embodiment RTE cereal is in the form of flakes that are created by using a cereal dough as prepared above and then forming the cooked cereal dough into pellets that have a desired moisture content. The pellets are then formed into wet flakes by passing the pellets through chilled roller and then subsequently toasting or heating the wet cereal flakes. The toasting causes a final drying of the wet flakes, resulting in slightly expanded and crisp RTE cereal flakes. The flakes are then screened for size uniformity. The final flake cereal attributes of appearance, flavor, texture, inter alia, are all affected by the selection and practice of the steps employed in their methods of preparation. For example, to provide flake cereals having a desired appearance feature of grain bits appearing on the flakes, one approach is to topically apply the grain bits onto the surface of the flake as part of a coating that is applied after toasting. Macronutrients and micronutrients may be provided during the manufacturing process to add essential vitamins and minerals to the product to create a well balanced, nutritionally complete meal.

In order to determine the amount of sterols, stanols, steryl esters, fatty acid derivatives or combinations thereof which are present in the sample and those that have been subsequently recovered by using by using a method set forth in commonly assigned application Ser. No. 10/172,390 filed Jun. 14, 2002 the disclosure of which including that found in the claims is incorporated herein by reference, the sample is subjected to gas chromatography. FIG. 1, illustrates the standard peaks for sterols.

Cooked starch-containing dough samples with increasing concentrations of amylopectin and fixed amounts of added steryl esters were assayed using the process described in the above referenced application.

The following table lists the results of exemplary RTE cereal samples prepared in connection with the process set forth above, which were tested after using the process described in the above referenced application. Example A lists values obtained using the preferred assay process identified in the above application.

TABLE 1

Sterol Determinations

| Sample Name | Sterol Target | Example A |
| --- | --- | --- |
| Batch Flake | 2.00 | 2.05 ± 0.16 |
| Clinical James Flake | 4.10 | 3.93 ± 0.2 |
| James Flake 1715 | 3.00 | 3.04 ± 0.12 |
| James Flake 1915 | 3.20 | 3.14 ± 0.05 |
| HSE Flake 11001 | 2.50 | 2.53 ± 0.01 |
| LSE Flake 12501 | 2.00 | 2.09 ± 0.05 |

Turning now to table 2 in which the first column represents the sample being tested. In this table, in addition to RTE cereals (batch flake and clinical test), a dough, which may be used for breads, muffins, rolls and other baked goods is also tested. The second column represent the sterol related compound based target (the amount of sterol in the food intermediate prior to processing), the third column measures the sterol present in the sample by using the process described in the aforementioned application and the fourth column represents the percent difference between the second and third columns.

TABLE 2

Sterol Determinations

| Sample Name | Sterol Target | Test A | % Difference |
| --- | --- | --- | --- |
| Brabender Var 1 | 2.32 | 2.38 ± 0.03 | 2.6 |
| Brabender Var 2 | 3.08 | 3.08 ± 0.14 | 2.0 |
| Brabender Var 3 | 3.71 | 3.98 ± 0.21 | 7.2 |
| Barbender Var 4 | 4.46 | 4.50 ± 0.06 | 0.8 |
| James Flake | 2.94 | 3.09 ± 0.16 | 5.1 |

It is believed that each of the foregoing tables illustrate the significant improvement of recovery of sterol related compounds from starch-containing food products or food components, when such starch containing compounds are bound in a polysaccharide complex, such as with amylopectin.

Figure 2:
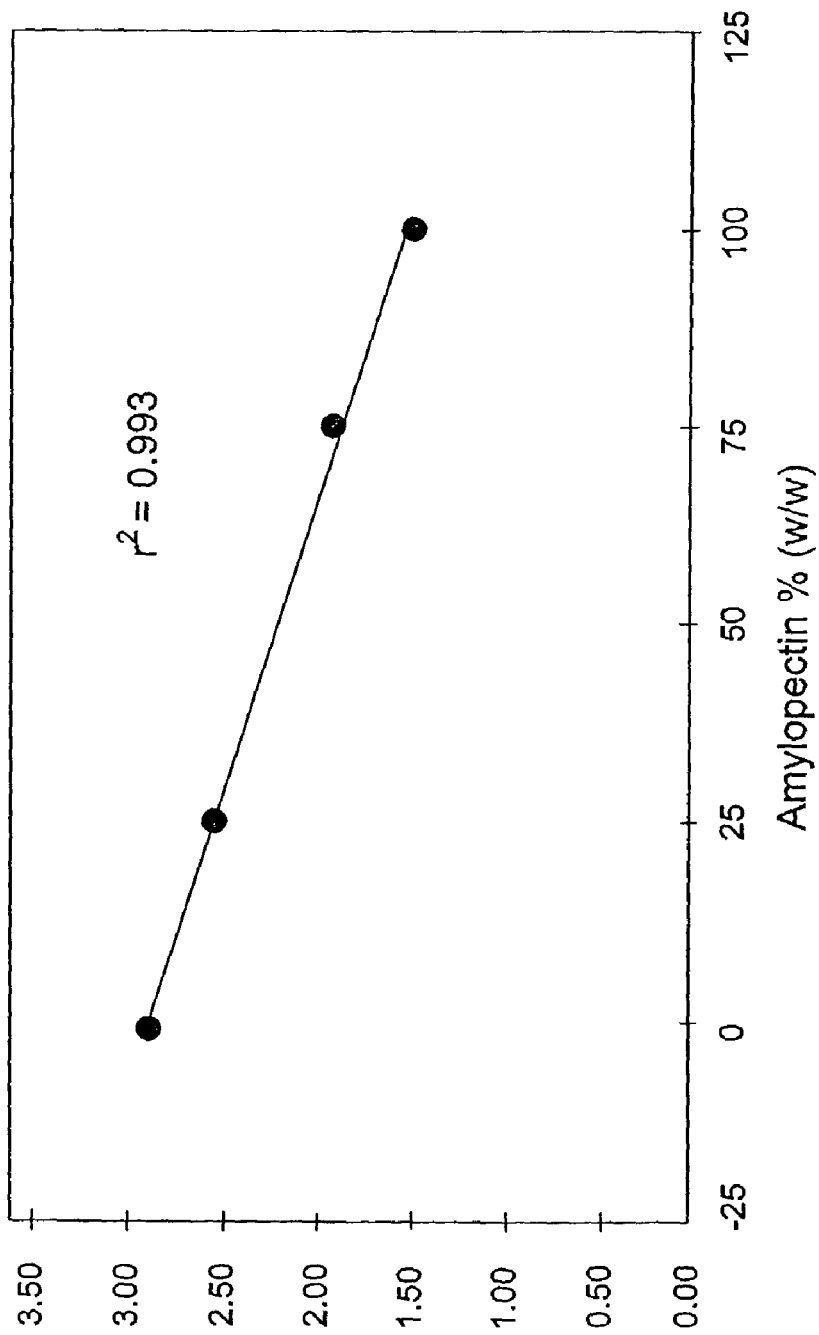
FIG. 2 is a graph showing the correlation of the level of sterol determined by the prior method to the amylopectin content of cooked doughs.

To illustrate the binding of phytosterol/phytosteryl ester to the amylopectin of starch, a fixed amount of phytosteryl esters was mixed with different starches of increasing amylopectin composition. FIG. 2 demonstrates that when the old industry standard sterol assay is used to assay the sterol content of the resulting dried doughs, the amount of sterol recovered was directly proportional to the amylopectin content of the starch. This indicates that an amylopectin-steryl ester complex is being formed which prevents phytosterol recovery by the old assay method.

Of course, regardless of the benefit provided by a product offering, if the product offering is not packaged in an aesthetically appealing manner or the product itself does not convey a suitable message, all the research and development, marketing, production, etc. is for naught, as the consumer will simply not purchase the product. Thus, it is important to communicate the value of the food intermediate of the present invention to the intended consumers.

In the present invention, the food intermediate was incorporated into a final food product. That food product may be an RTE cereal, meal, baked goods, such as rolls, biscuits or breads, snack foods or the like. That product is then introduced into a clinical or other study during which the food product is provided to a number of test participants. During the study, the participants ingest the food product, are weighed, submit biological samples answer questionnaires about the product and provide other useful information. Once the study is complete, the results are collected and presumably, the benefit of the food product is confirmed.

Once the results of the study are known, then a communication message is drafted. The message will be prepared in connection with what is permissible in light of the various regulatory guidelines, Generally Recognized as Safe (GRAS) status and other relevant criteria. Once the message has been developed it is then printed or imaged on the product packing or communicated via other advertising media to alert the consumers to the benefit of the product. Suitable advertising means may include print, such as newspapers, magazines, journals and other publications, audio and/or visual means such as radio and television, free sampling and the like.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

The invention claimed is:

1. A method of making a food intermediate having enhanced cholesterol-uptake inhibition comprising the steps of;
   a) providing a source of amylopectin;
   b) providing a phytosteryl ester;
   c) preparing a mixture consisting essentially of the source of amylopectin and the phytosteryl ester;
   d) heating the mixture to create a complex containing phytosteryl ester bound to amylopectin; and
   e) subsequently adding the complex to other pre-selected ingredients in an amount effective to make a food intermediate having enhanced cholesterol-uptake inhibition.

2. The method of claim 1, wherein the complex is dried prior to addition to other pre-selected ingredients to make the food intermediate.

3. The method of claim 1, wherein the mixture is formed in an aqueous solution.

4. The method of claim 1, wherein the mixture is a neat mixture.

5. The method of claim 1, wherein the source of phytosteryl ester is selected from the group consisting of fatty acid derivatives of β-sitosterol, stigmasterol, ergosterol, campesterol, β-sitostanol, campestanol and stigmastanol.

6. The method of claim 1, wherein the food intermediate is a grain based dough.

7. The method of claim 6, wherein the grain based dough is used to make an RTE cereal.

8. The method of claim 6, wherein the grain based dough is used to make bread.

* * * * *